US007271387B2

United States Patent
Chou et al.

(10) Patent No.: US 7,271,387 B2
(45) Date of Patent: Sep. 18, 2007

(54) LASER DESORPTION AND THERMAL EMISSION SPECTROSCOPY FOR CHEMICAL ANALYSIS OF CRYOGENIC SURFACES

(75) Inventors: Mau-Song Chou, Rancho Palos Verdes, CA (US); Jonathan W. Arenberg, Santa Monica, CA (US); Andy Christensen, Fountain Valley, CA (US); Luke Sollitt, Pasadena, CA (US)

(73) Assignee: Northrop Grumman Corporation, Los Angeles, CA (US)

( * ) Notice: Subject to any disclaimer, the term of this patent is extended or adjusted under 35 U.S.C. 154(b) by 29 days.

(21) Appl. No.: 11/227,574

(22) Filed: Sep. 14, 2005

(65) Prior Publication Data

US 2007/0057188 A1    Mar. 15, 2007

(51) Int. Cl.
*G01J 5/02*    (2006.01)

(52) U.S. Cl. .................................................. 250/341.1

(58) Field of Classification Search .............. 250/341.1
See application file for complete search history.

(56) References Cited

U.S. PATENT DOCUMENTS

| | | | | |
|---|---|---|---|---|
| 5,171,989 A | * | 12/1992 | Williams et al. | ............ 250/288 |
| 6,531,701 B2 | | 3/2003 | Chou et al. | |
| 2004/0114130 A1 | * | 6/2004 | Nguyen et al. | ................ 356/36 |
| 2004/0259234 A1 | | 12/2004 | Chou et al. | |
| 2005/0026276 A1 | | 2/2005 | Chou | |
| 2005/0056785 A1 | | 3/2005 | Chou et al. | |

* cited by examiner

*Primary Examiner*—David Porta
*Assistant Examiner*—Marcus Taningco
(74) *Attorney, Agent, or Firm*—Tarolli, Sundheim, Covell & Tummino LLP

(57) ABSTRACT

A method for remote analysis of materials embedded in a frozen surface, such as in the icy surface of a planetary body. A laser on board a spacecraft irradiates the frozen surface and thereby releases materials in a gas cloud, by a process of desorption. The laser wavelength is selected to maximize the release of substances by the desorption process, which does not fragment materials into their elemental components. An infrared (IR) spectrometer on the spacecraft detects thermal emissions from the gas cloud against a background provided by the frozen surface, and can readily identify a variety of organic, inorganic and biological materials from their thermal spectra.

8 Claims, 1 Drawing Sheet

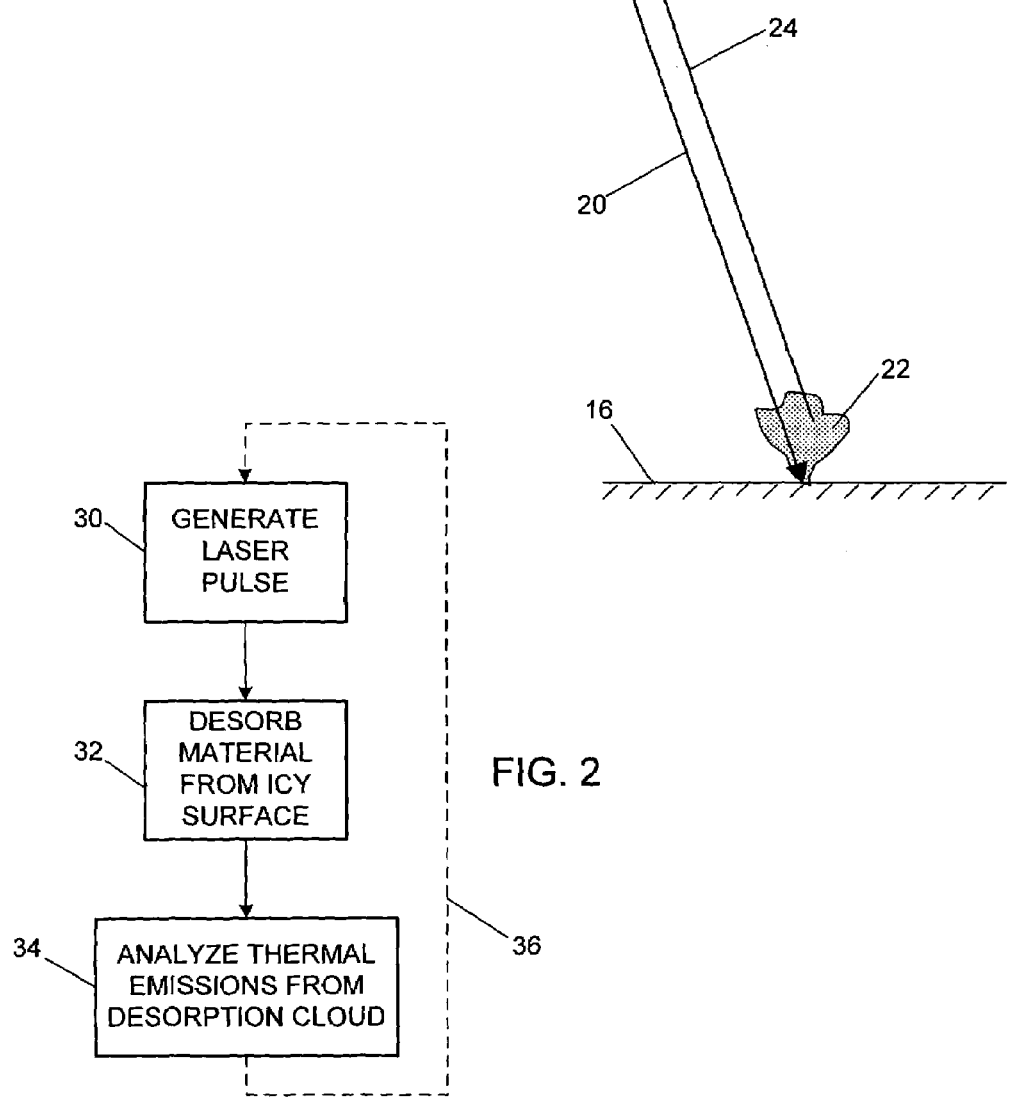

LASER DESORPTION AND THERMAL EMISSION SPECTROSCOPY FOR CHEMICAL ANALYSIS OF CRYOGENIC SURFACES

BACKGROUND OF THE INVENTION

This invention relates generally to remote chemical and biological analysis and, more particularly, to remote analysis of materials contained within cryogenic surfaces. An application of particular interest is the remote exploration of planets and their moons. The US National Aeronautics and Space Administration (NASA) is planning a Jupiter Icy Moons Orbiter (JIMO) to explore the nature and extent of habitable environments in the solar system. One of the main objectives of the mission is to detect and analyze a wide variety of chemical species, including chemical elements, salts, minerals, organic and inorganic compounds, and possible biological compounds, in the surface of Jupiter's icy moons.

One possible technique for analysis of icy moon surfaces is laser-induced breakdown spectroscopy (LIBS), in which a powerful laser beam is used to ablate material from a surface area of interest. A spectrometer is used to analyze electromagnetic emissions that ensue during a very brief time interval following ablation of the surface material. Many materials can be identified by this technique because all elements emit light when excited to sufficiently high temperatures. The only limitations are the power of the laser and the sensitivity and frequency range of the detector and spectrometer. The most significant drawback of using LIBS for exploration and analysis of planetary bodies is that a laser irradiance of about 1 GW/cm2 is required. Even in a space vehicle with relatively high internal power generation resources, such as onboard nuclear power, using a laser this powerful is a practical impossibility. The LIBS technique is further limited to analysis of chemical elements. Chemical compounds become fragmented under a plasma breakdown condition that is inherent in the ablation process.

Remote analysis of gas and aerosol clouds is a relatively well known technology. For example, U.S. Pat. No. 6,531,701 to Mau-Song Chou et al., entitled "Remote Trace Gas Detection and Analysis" and Patent Application Publication No. US 2005/0026276, by Mau-Song Chou, entitled "Remote Detection and Analysis of Chemical and Biological Aerosols," both disclose techniques for remotely analyzing a cloud based on spectroscopic observation of thermal emissions from the cloud as a result of a radiation beam. These techniques cannot, of course, be used directly to analyze materials that are bound to an ice matrix.

It is also known in the art that thermal spectral analysis of gases or aerosols may be enhanced by placing a cold device such that it serves as a background in the field of view of the spectrometer. Patent Application Publication No. US 2004/0259234, by Mau-Song Chou et al., entitled "Detection and Analysis of Chemical and Biological Materials," and Patent Application No. US 2005/0056785, by Mau-Song Chou et al., entitled "Detection and Analysis of Chemical and Biological Materials by Passive Emission of Terahertz Wave Against a Cold Background Target," both describe devices in which this technique is used.

Although the spectral analysis of thermal emissions from a gas or aerosol cloud are known in the art, this type of analysis cannot be directly applied to materials contained within an ice matrix. Prior to this invention, the only known approach to releasing materials from the ice matrix was to use the LIBS technique mentioned above. Since the LIBS technique does not preserve molecular structures and since the technique requires impractically large laser power levels, there is a need for an alternative approach for releasing and analyzing material that is bound in an ice matrix, particularly one at cryogenic temperatures. The present invention provides a convenient solution to this problem.

SUMMARY OF THE INVENTION

The present invention resides in a method for remotely releasing materials from an ice matrix and analyzing their content by means of thermal emission spectroscopy. Briefly, and in general terms, the method of the invention comprises the steps of irradiating a selected area of the ice matrix with a laser beam that provides a surface fluence level sufficient to release materials from the ice matrix and form a desorbed plume of these materials in gas or vapor states; receiving thermal emissions from the desorbed plume; and performing a spectral analysis of the received thermal emissions to identify materials in the desorbed plume.

More specifically, the ice matrix is typically located on the surface of a planetary body; and the steps of the method are performed under control of a spacecraft orbiter. The method typically further comprises repeating the steps of irradiating, receiving and performing a spectral analysis, at successive locations on the icy surface, as the spacecraft orbiter moves over the surface.

In a disclosed embodiment of the method, the step of irradiating employs a laser beam having a wavelength of approximately 3 μm and the step of irradiating provides a surface fluence greater than a threshold value of approximately 120 mJ/cm2. Further, the step of irradiating employs a pulsed laser beam, with a pulse width of approximately 3 μs.

It will be appreciated from this summary that the method of the invention provides a previously unknown technique for chemical and biological analysis of materials embedded in a remote and icy surface, using a combination of laser desorption and thermal emission spectroscopy. Other aspects and advantages of the invention will become apparent from the following more detailed description, taken in conjunction with the accompanying drawings.

BRIEF DESCRIPTION OF THE DRAWINGS

FIG. 1 is diagram depicting the principle of the present invention.

FIG. 2 is a block diagram showing steps performed in accordance with the method of the invention.

DETAILED DESCRIPTION OF THE INVENTION

As shown in the drawings for purposes of illustration, the present invention is concerned with a technique for remotely analyzing materials contained within an ice matrix, which may exist at cryogenic temperatures. Releasing materials from a remotely located ice matrix has proved to be an elusive goal, principally because of the high power levels that seemed to be needed. Use of laser induced breakdown spectroscopy (LIBS) not only requires impractically high powers but has the further drawback that it results in fragmentation of chemical compounds into elemental components. Even the use of laser desorption to release materials for analysis has been thought to require impractically high fluence levels.

In accordance with the present invention, release of materials from an ice matrix is achieved by laser desorption at attainable fluence levels. The desorption results in formation of a cloud of the released materials, which is then analyzed by the known techniques of thermal emission spectroscopy.

As shown in FIG. 1, a spacecraft orbiter vehicle 10 includes a laser source 12 and spectrometer 14. When the orbiter 10 is in an appropriate position above the surface 16 of an icy moon or some other planetary body, the laser 12 is commanded to direct a pulsed radiation beam 20 to a desired region of the icy surface. As a result of a desorption process, material is released from the surface in a cloud or plume 22 of desorbed material in the gas state. At an appropriate time after the start of a pulse from the laser source 12, the spectrometer 14 is activated to begin sensing thermal radiation received from the plume 22. Because the plume 22 is viewed by the spectrometer 14 against the very cold background of an icy moon, the received thermal emissions are unambiguously representative of the materials contained in the plume.

Laser desorption is known to involve an explosive phase-transition process. Micro-cavitations or bubbles may be formed near the surface layer, as induced by the deposition of the laser energy. Rupture or collapse of such micro-bubbles thus forms energetic processes that explosively remove a layer from the surface material into the gas phase. The nature of desorption is such that desorbed materials remain nearly intact, with minimal fragmentation. In particular, there is no fragmentation of chemical compounds into their constituent elements.

Thermal emission spectroscopy performed in the spectrometer 14 generally follows the principles described in the aforementioned U.S. Pat. No. 6,531,701 and Patent Application Publication No. US 2005/0026276. Because the thermal emissions are viewed against the background of the icy surface 16, the spectrographic analysis is further facilitated, as taught by the aforementioned Patent Application Publication Nos. US 2004/0259234 and US 2005/0056785.

FIG. 2 diagrammatically depicts the method steps of the invention, including the steps of generating a laser pulse, as indicated in block 30, desorbing material from the icy surface 16 to which the laser pulse is directed, as indicated in block 32, and spectrographically analyzing thermal emissions from the desorbed plume 22 of material, as indicated in block 34. In practice, these steps would be performed repeatedly, as indicated by the broken line 36, to analyze a desired region on the icy surface 16. A succession of laser pulses may be directed to a strip on the surface 16 corresponding to the path traced by the laser beam as the orbiter 10 moves in relation to the surface. Alternatively, the laser pulses may be deflected by mirrors or other means, to impact a desired succession of regions on the surface 16.

An infrared (IR) laser at a relatively mild fluence appears to be capable of desorbing chemical compounds in ice into the gas phase. Based on experiments using photoacoustic spectroscopy (PAS) to determine the threshold for laser desorption of ice, it appears that the threshold fluence for desorption of ice with a laser wavelength of near 3.1 μm (the wavelength at which desorption yield from ice is known to peak) is near 120 mJ/cm$^2$, and not a much higher value suggested in some of the technical literature. In addition, the desorbed vapors have been shown experimentally to be much warmer than the ice. Therefore, a thermal emission spectroscopic technique can be used to measure the warmer vapor against the colder ice surface, by use of an IR spectrometer or an IR spectral imager as the spectrometer 14 aboard the spacecraft 10. The emission spectra observed by the spectrometer 14 are expected to be in the range of 5 to 25 μm in wavelength and can provide fingerprint-signatures for identification and analysis of many chemicals of interest. These include inorganic compounds such as $H_2O_2$, CO, $CO_2$, $SO_2$, NO, $NO_2$, $(CN)_2$, $NH_3$, $H_2(CO_3)_2$, $NaSO_4$ and $H_2SO_4$; organic compounds such as $CH_4$, $C_2H_2$, $C_2H_4$, tholins and sulphonic/sulphinic acids; and biological materials such as protein, DNA, RNA, and bacteria.

As mentioned above, the optimal laser wavelength for the laser desorption appears to be near 3.1 μm, which is the peak of optical absorption of the ice at ~100° K. An OPO (optical parametric oscillated) laser may be tuned to this wavelength. Alternatively, a compact Er:YAG (erbium:yttrium-aluminum-garnet) laser at 2.94 μm can be used, although the desorption yield is likely to be reduced by about 50% from that at 3.1 μm, because of a lower absorption coefficient resulting from use of the different wavelength. Based on a threshold fluence of 120 mJ/cm$^2$ and use of an IR laser at ~3.1 μm, one can estimate an operational laser fluence of about 240 mJ/cm$^2$, which is taken to be about twice of the threshold. A relatively long laser pulse width up to 3 μs may be used to produce a required irradiance.

The spot size of the laser beam is estimated to be about 30 cm for a 3-μm laser source located at an altitude of 100 km, assuming a one-meter telescope is used for beam delivery. Hence the required pulse energy is estimated to be ~170 J with a corresponding laser irradiance is ~5.7×10$^7$ W for a pulse width of ~3 μs. A deployable telescope of several meters can reduce the laser spot size, thereby also reducing the required laser energy. For example, a laser-pulse energy of 6.8 J with a corresponding power of 2.3×10$^6$ W is needed for the desorption if a five-meter telescope is employed.

The detection sensitivity is expected to be exceptionally high, due to a large thermal contrast between the desorbed vapors and a cold surface and the presence of an extremely low emission background from the cold surface. The desorbed vapors are expected to be near 300° K., while the surface temperature is very low, for example a daily temperature of about 85° to 125° K. on the surface of Europa.

It will be appreciated from the foregoing that the present invention represents a significant advance in techniques for remote chemical and biological analysis, particularly as applied to space exploration. The combination of laser desorption and thermal emission spectroscopy allows the analysis of ice-bound materials without their fragmentation into elemental components. It will also be appreciated that, although a specific embodiment of the invention has been described in detail for purposes of illustration, various modifications may be made without departing from the spirit and scope of the invention. Accordingly, the invention should not be limited except as by the appended claims.

The invention claimed is:

1. A method for analyzing materials bound to an ice matrix on a surface of a planetary body, the method comprising:

irradiating a selected area of the ice matrix on the surface of the planetary body with a laser beam that provides a surface fluence level sufficient to release materials from the ice matrix and form a desorbed plume of these materials in gas or vapor states;

receiving thermal emissions from the desorbed plume; and performing a spectral analysis of the received thermal emissions to identify materials in the desorbed plume.

2. A method as defined in claim 1, wherein;
the steps of the method are performed on a spacecraft orbiter.

3. A method as defined in claim 2, and further comprising:
repeating the steps of irradiating, receiving and performing a spectral analysis at successive locations on the icy surface, as the spacecraft orbiter moves over the surface.

4. A method as defined in claim 1, wherein the step of irradiating employs a laser beam having a wavelength of approximately 3 μm.

5. A method as defined in claim 4, wherein the step of irradiating provides a surface fluence greater than a threshold value of approximately 120 mJ/cm$^2$.

6. A method as defined in claim 1, wherein the step of performing spectral analysis employs an infrared (IR) spectrometer.

7. A method as defined in claim 1, wherein the step of irradiating employs a pulsed laser beam.

8. A method as defined in claim 7, wherein the laser beam has a pulse width of approximately 3 μs.

* * * * *